(12) United States Patent
McGuckin, Jr. et al.

(10) Patent No.: US 7,992,565 B2
(45) Date of Patent: *Aug. 9, 2011

(54) FALLOPIAN TUBE OCCLUSION DEVICE

(75) Inventors: James F. McGuckin, Jr., Radnor, PA (US); David M. Schaller, Wallingfodrd, CT (US); James Erich Bressler, Langhorne, PA (US)

(73) Assignee: Rex Medical, L.P., Conshohocken, PA (US)

( * ) Notice: Subject to any disclaimer, the term of this patent is extended or adjusted under 35 U.S.C. 154(b) by 197 days.

This patent is subject to a terminal disclaimer.

(21) Appl. No.: 12/151,953

(22) Filed: May 9, 2008

(65) Prior Publication Data

US 2008/0302368 A1    Dec. 11, 2008

Related U.S. Application Data

(60) Provisional application No. 60/932,405, filed on May 31, 2007.

(51) Int. Cl.
*A61F 6/20* (2006.01)
*A61F 6/06* (2006.01)

(52) U.S. Cl. ........ 128/831; 128/830; 128/887; 606/193; 606/198; 606/200; 604/104

(58) Field of Classification Search .......... 128/830, 128/831, 898, 843, 887; 606/157, 200, 191–199; 604/104–107
See application file for complete search history.

(56) References Cited

U.S. PATENT DOCUMENTS

| | | |
|---|---|---|
| 3,744,492 A | 7/1973 | Leibinsohn |
| 4,266,815 A | 5/1981 | Cross |
| 4,832,055 A | 5/1989 | Palestrant |
| 5,059,205 A | 10/1991 | El-Nounou et al. |
| 5,709,704 A | 1/1998 | Nott et al. |
| 6,059,825 A | 5/2000 | Hobbs et al. |
| 6,126,673 A | 10/2000 | Kim et al. |
| 6,152,144 A | 11/2000 | Lesh et al. |
| 6,235,044 B1 | 5/2001 | Root et al. |
| 6,355,051 B1 | 3/2002 | Sisskind et al. |
| 6,436,120 B1 | 8/2002 | Meglin |
| 6,506,205 B2 | 1/2003 | Goldberg et al. |
| 6,551,303 B1 | 4/2003 | VanTassel et al. |
| 6,599,307 B1 | 7/2003 | Huter |
| 6,605,102 B1 | 8/2003 | Mazzocchi et al. |
| 6,652,555 B1 | 11/2003 | VanTassel et al. |
| 6,652,556 B1 | 11/2003 | VanTassel et al. |
| 6,660,021 B1 | 12/2003 | Palmer et al. |
| 6,689,150 B1 | 2/2004 | VanTassel et al. |
| 6,811,560 B2 | 11/2004 | Jones et al. |
| 6,890,340 B2 | 5/2005 | Duane |
| 6,932,831 B2 | 8/2005 | Forber |

(Continued)

FOREIGN PATENT DOCUMENTS

EP    1707233    4/2006

(Continued)

*Primary Examiner* — Patricia M Bianco
*Assistant Examiner* — Keri J Nelson
(74) *Attorney, Agent, or Firm* — Neil D. Gershon

(57) ABSTRACT

A device for occluding the fallopian tube including a retention member and a mesh material supported by the retention member. The retention member has a first lower profile configuration for delivery and a second expanded configuration for placement within the fallopian tube. The mesh material is configured to block passage of an egg through the tube. The member has a plurality of tube engagement members to secure the retention member to the fallopian tube.

2 Claims, 10 Drawing Sheets

U.S. PATENT DOCUMENTS

| | | |
|---|---|---|
| 6,941,169 B2 | 9/2005 | Pappu |
| 6,958,074 B2 | 10/2005 | Russell |
| 6,989,021 B2 | 1/2006 | Bosma et al. |
| 6,994,092 B2 | 2/2006 | van der Burg et al. |
| 6,994,717 B2 | 2/2006 | Kónya et al. |
| 7,025,756 B2 | 4/2006 | Frazier et al. |
| 7,037,321 B2 | 5/2006 | Sachdeva et al. |
| 7,044,134 B2 | 5/2006 | Khairkhahan et al. |
| 7,097,651 B2 | 8/2006 | Harrison et al. |
| 7,097,652 B2 | 8/2006 | Becker et al. |
| 7,115,110 B2 | 10/2006 | Frazier et al. |
| 7,128,073 B1 | 10/2006 | van der Burg et al. |
| 6,972,025 B2 | 12/2006 | WasDyke |
| 7,169,164 B2 | 1/2007 | Borillo et al. |
| 7,220,271 B2 | 5/2007 | Clubb et al. |
| 7,316,708 B2 | 1/2008 | Gordon |
| 2002/0029051 A1* | 3/2002 | Callister et al. ............... 606/157 |
| 2002/0193828 A1 | 12/2002 | Griffin et al. |
| 2003/0181942 A1 | 9/2003 | Sutton et al. |
| 2003/0195555 A1 | 10/2003 | Khairkhahan et al. |
| 2004/0044361 A1 | 3/2004 | Frazier et al. |
| 2004/0093016 A1 | 5/2004 | Root et al. |
| 2004/0111111 A1 | 6/2004 | Lin |
| 2005/0027314 A1 | 2/2005 | WasDyke |
| 2005/0165441 A1 | 7/2005 | McGuckin, Jr. et al. |
| 2005/0165442 A1 | 7/2005 | Thinnes, Jr. et al. |
| 2005/0203568 A1 | 9/2005 | Burg et al. |
| 2005/0267515 A1 | 12/2005 | Oliva et al. |
| 2006/0015136 A1 | 1/2006 | Besselink |
| 2006/0079928 A1 | 4/2006 | Cartier et al. |
| 2006/0155165 A1 | 7/2006 | Vanden Hoek et al. |
| 2006/0287670 A1 | 12/2006 | Pal |
| 2007/0088381 A1 | 4/2007 | McGuckin, Jr. et al. |
| 2007/0213685 A1 | 9/2007 | Bressler et al. |

FOREIGN PATENT DOCUMENTS

| | | |
|---|---|---|
| FR | 2567405 | 1/1986 |
| JP | 2005 324019 | 11/2005 |
| WO | 2005 034764 | 4/2005 |
| WO | 2005 074844 | 8/2005 |

* cited by examiner

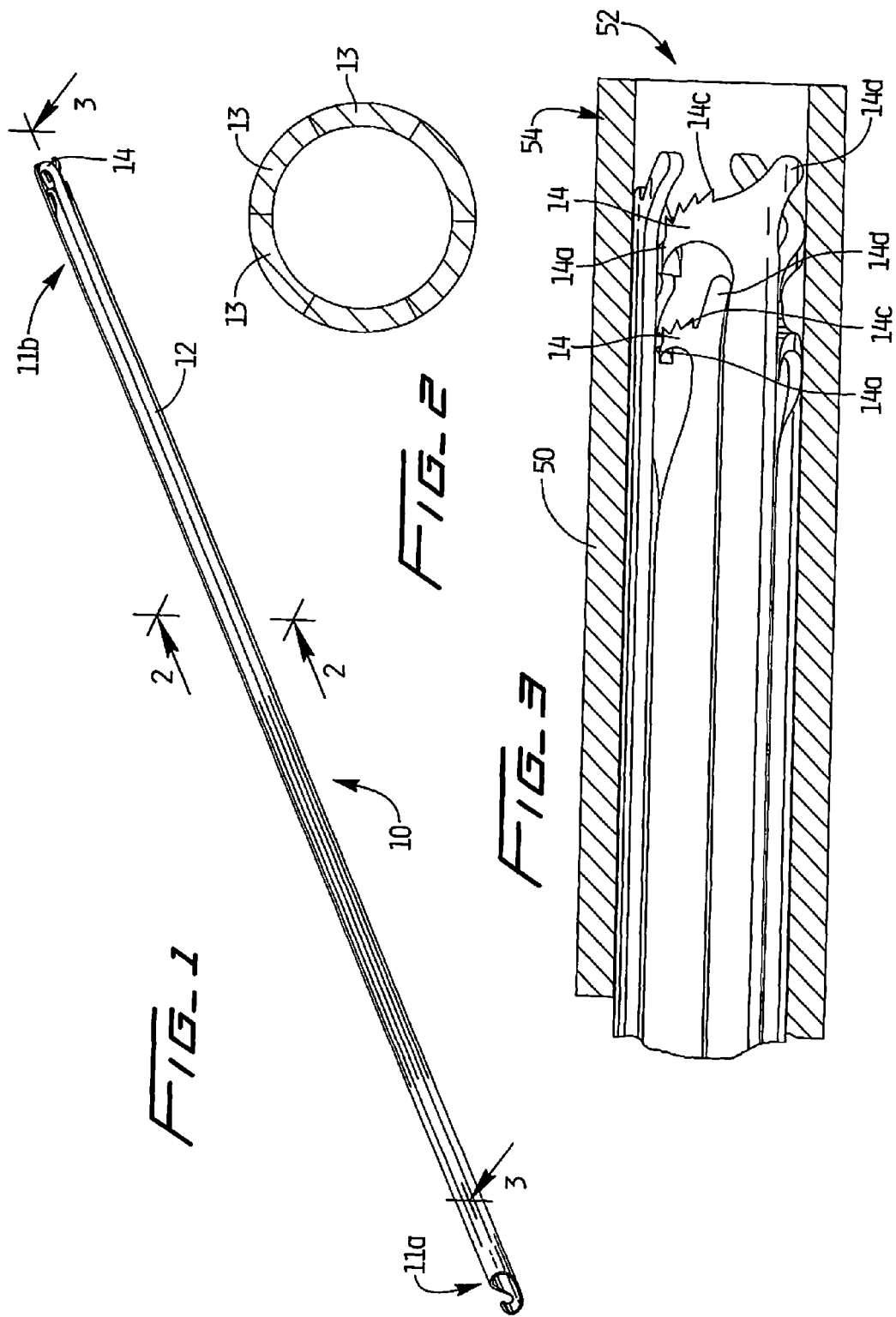

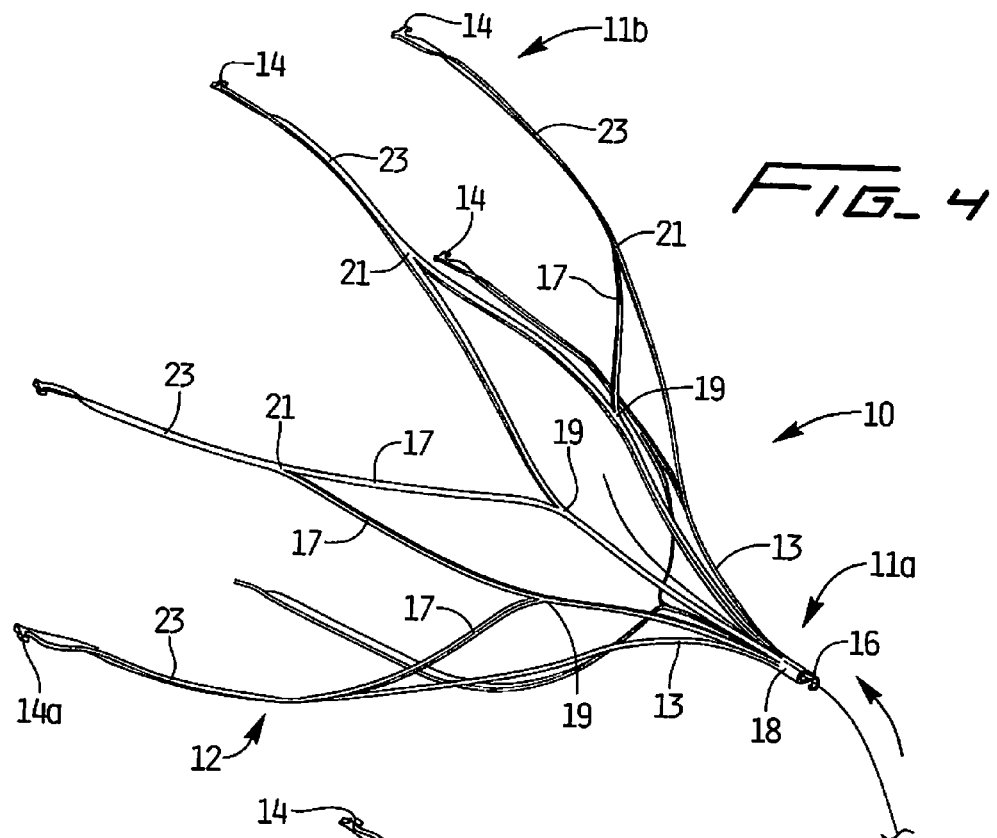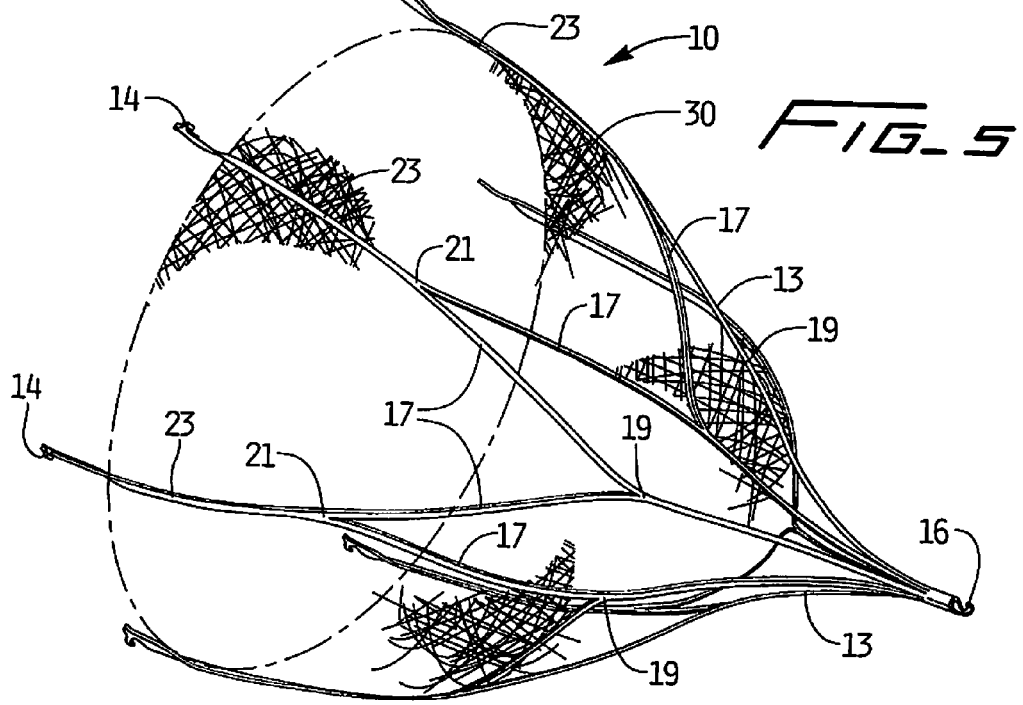

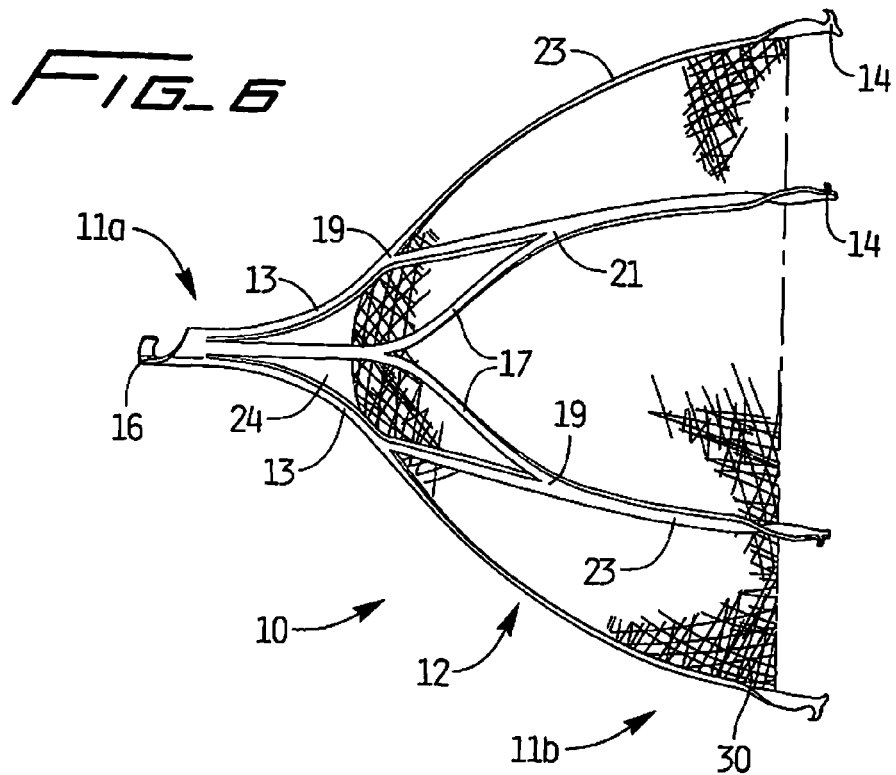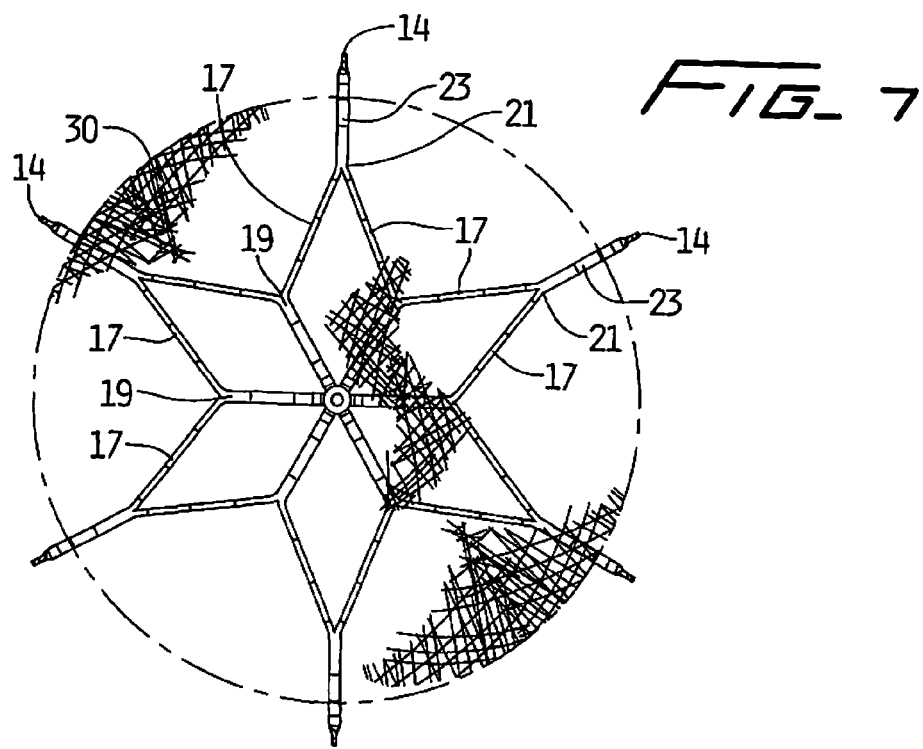

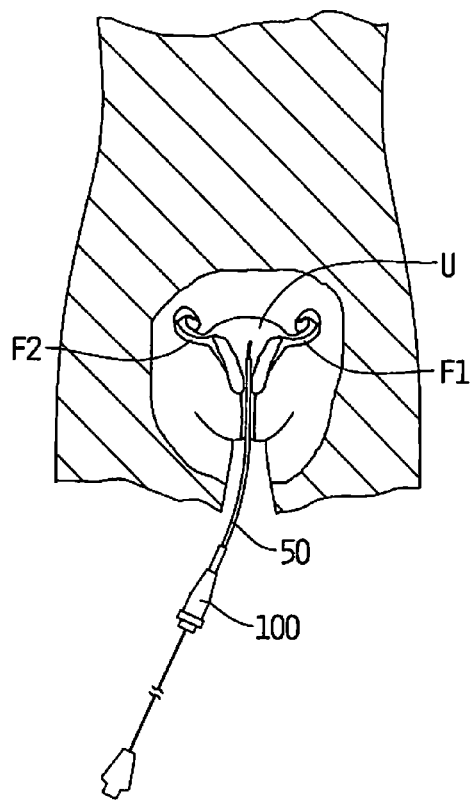
FIG_8
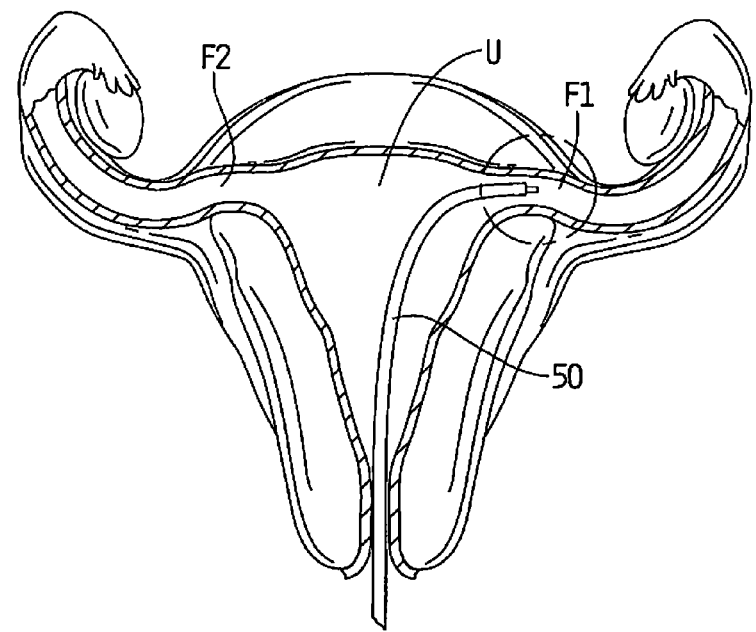
FIG_9

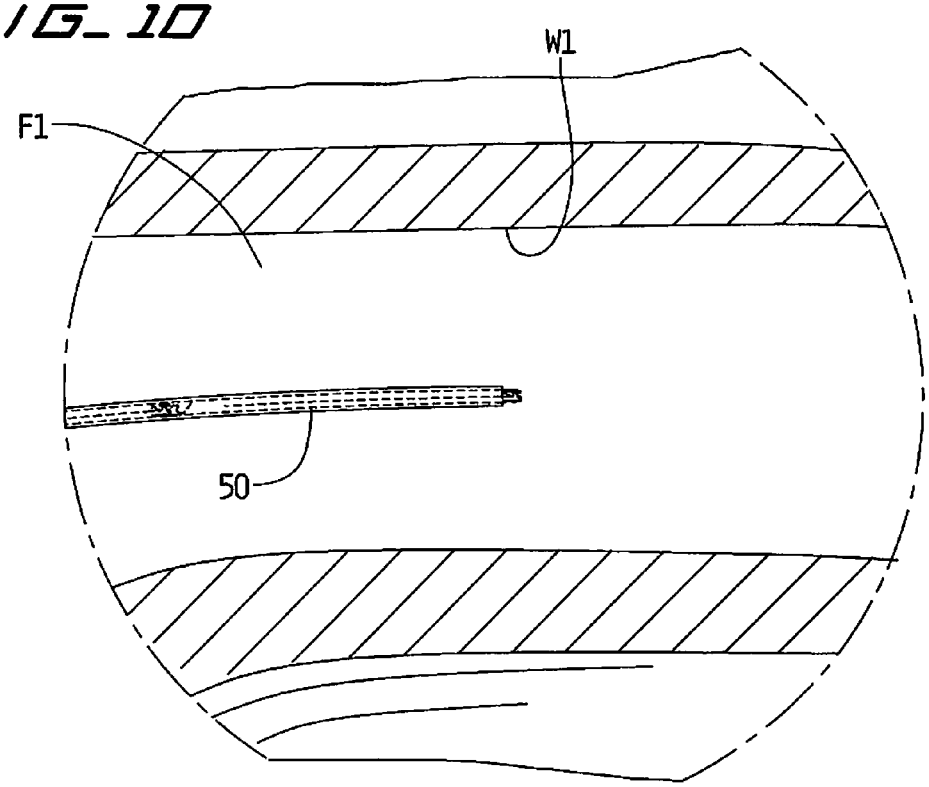
FIG_10
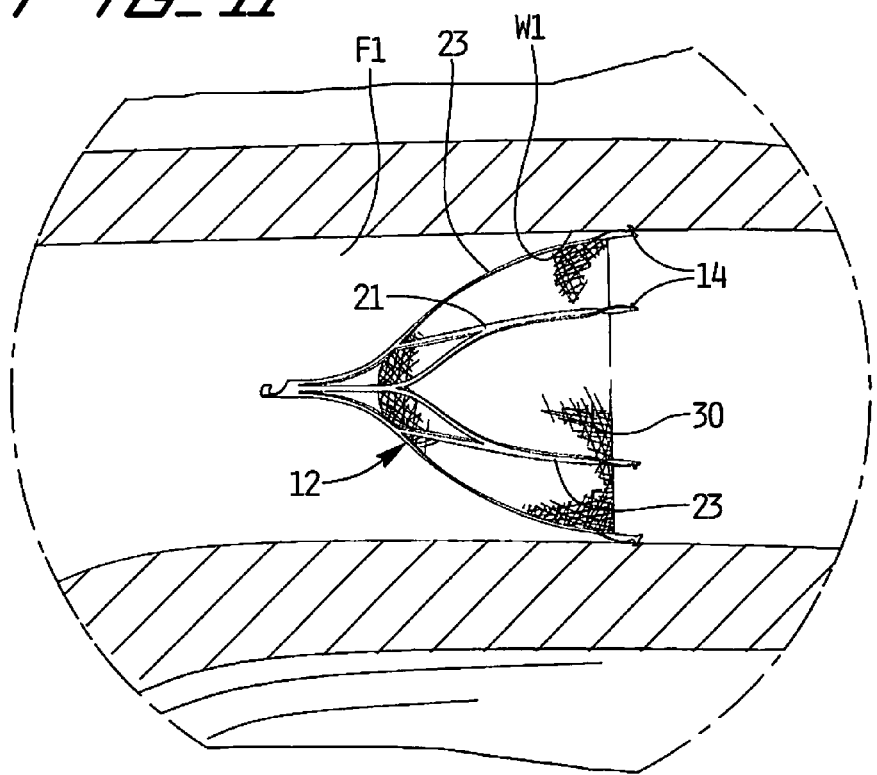
FIG_11

FIG_14
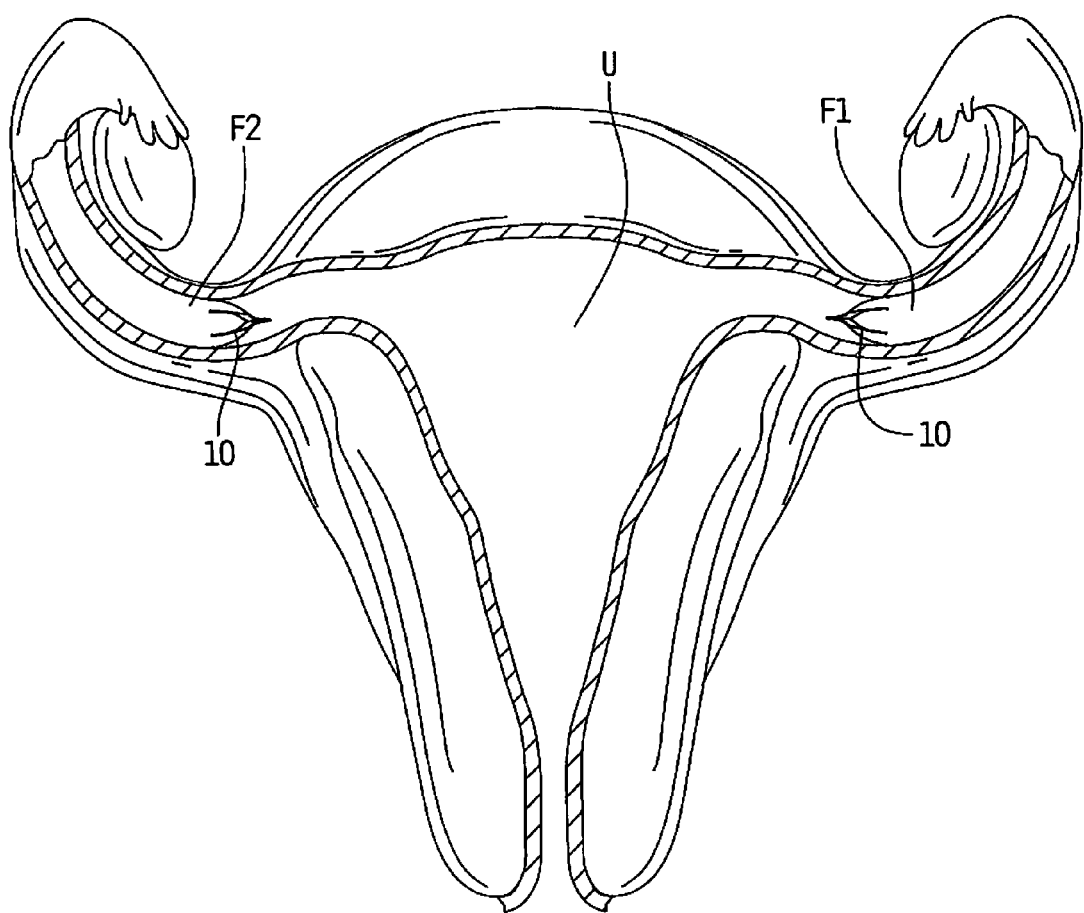

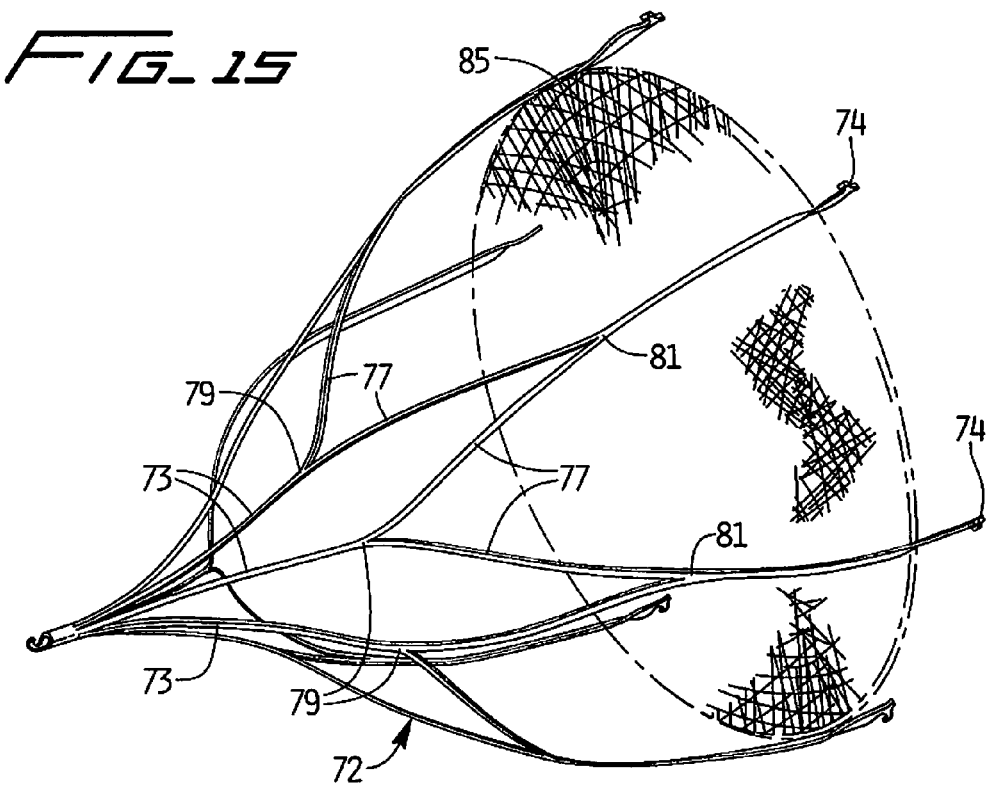
FIG_15
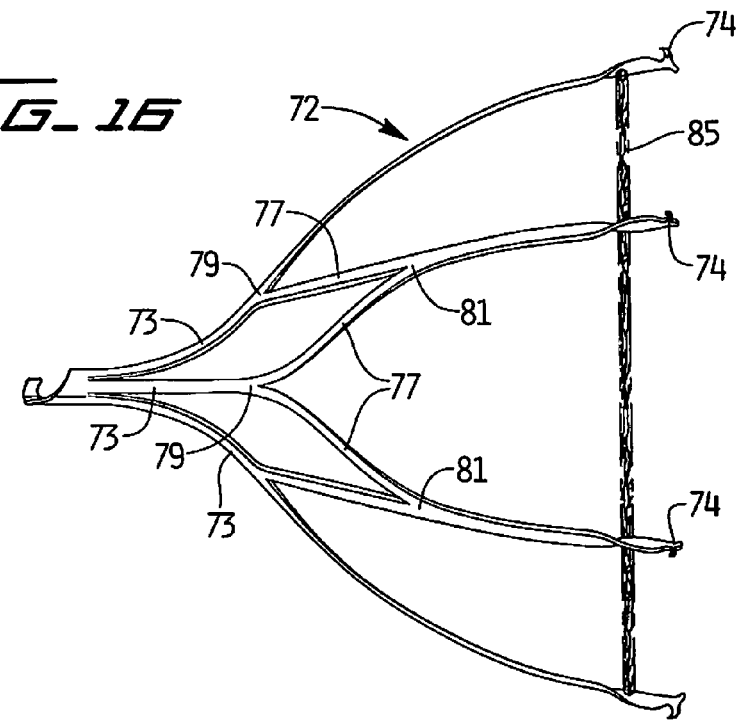
FIG_16

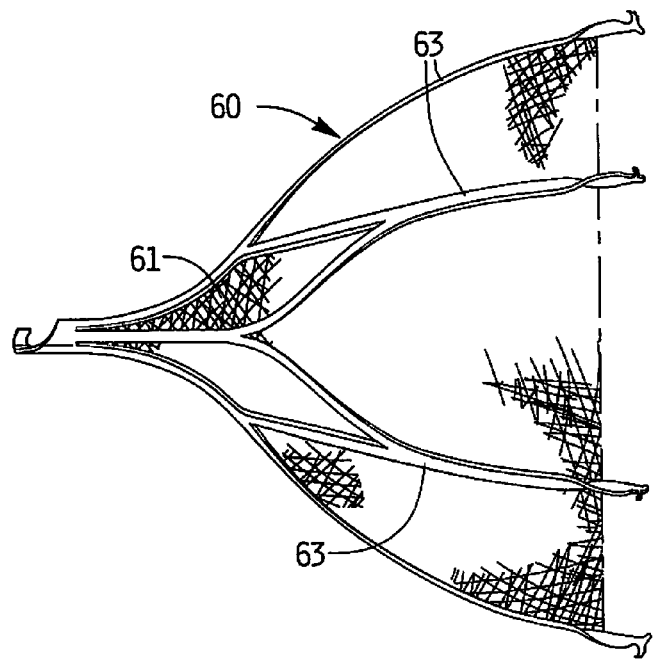
FIG_17
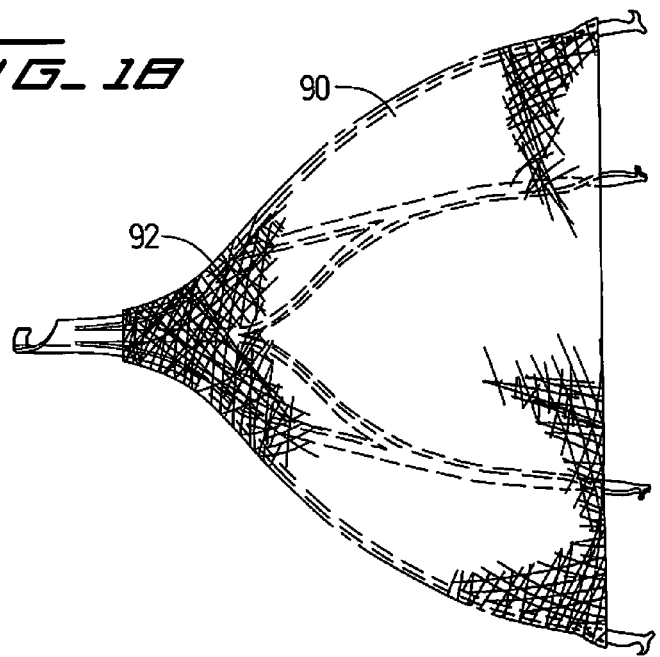
FIG_18

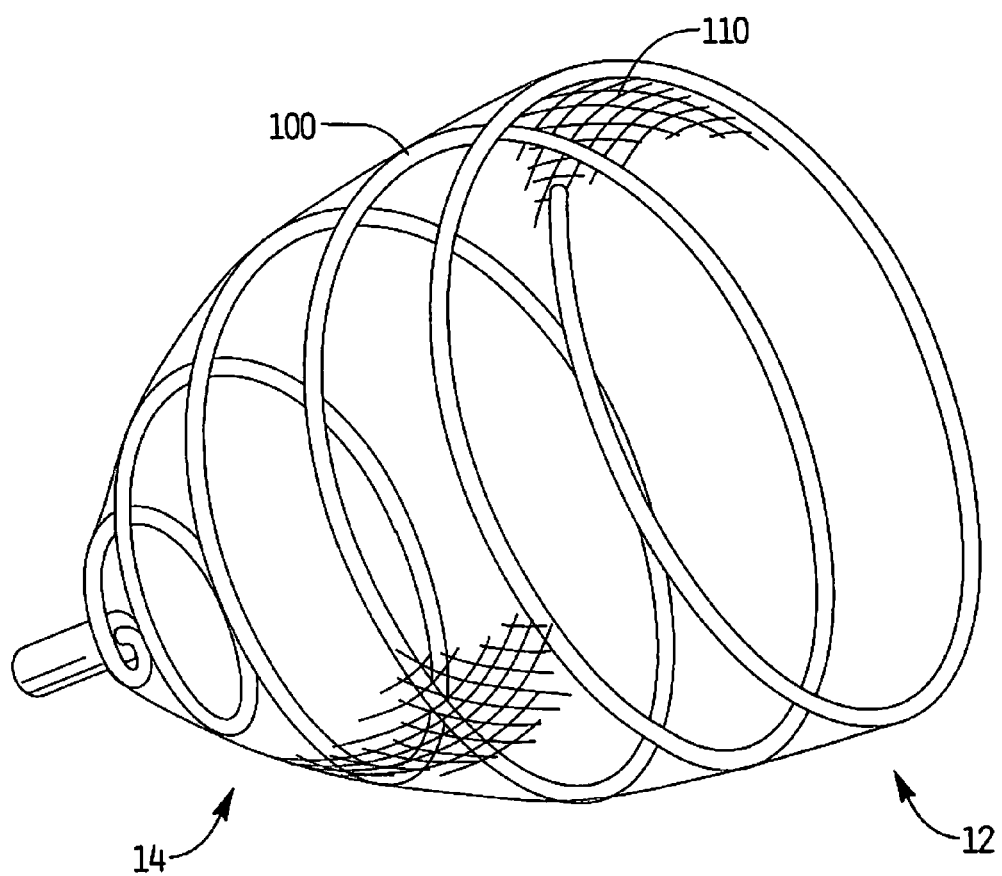
FIG_19

FALLOPIAN TUBE OCCLUSION DEVICE

This application claims priority from provisional application Ser. No. 60/932,405 filed May 31, 2007, the entire contents of which is incorporated herein by reference.

BACKGROUND

1. Field of the Invention

This application relates to a minimally invasive device for occluding the fallopian tubes.

2. Background of Related Art

Tubal ligation is one method of female sterilization. It can be performed laparoscopically by access through the patient's abdomen where the surgeon severs and closes the ends of the fallopian tubes by tying, applying clamps or cauterization. These devices achieve occlusion by external application to the tube.

Other methods involve transcervical access. In some techniques, various agents are injected within each of the fallopian tubes to close or block the tubes. In other transcervical procedures, mechanical devices are inserted and anchored within the tube to promote tissue ingrowth and scar tissue formation to occlude the tubes. In other techniques, radiofrequency energy electrodes are inserted and energized to thermally damage the tube, causing scarring to occlude it.

The need exists for an improved device for occluding the fallopian tubes which can be inserted in a minimally invasive fashion.

SUMMARY

The present invention overcomes the problems and deficiencies of the prior art. The present invention provides a device for occluding the fallopian tube comprising a retention member and a mesh material supported by the retention member. The retention member has a first lower profile configuration for delivery and a second expanded configuration for placement within the fallopian tube. The mesh material is configured to block passage of an egg through the fallopian tube. The retention member has a plurality of fallopian tube engagement members to secure the retention member to the fallopian tube.

In one embodiment, the mesh is attached to an outer surface of the retention member. In another embodiment, the retention member has a plurality of struts defining a space therebetween and the mesh fills a substantial region of the space. In another alternate embodiment, the mesh is a strip of material connected to the retention member and spanning an opening of the retention member. In this embodiment, the mesh is preferably positioned at a region adjacent the tube engagement members. In a preferred embodiment, the retention member is composed of shape memory material.

The tube engagement members may include a plurality of teeth. In a preferred embodiment, the retention member has a plurality of struts and the struts terminate in the tube engagement members. In a preferred embodiment, the retention member is composed of shape memory material.

The present invention also provides a device for occluding the fallopian tube comprising a tube laser cut to form a series of struts, wherein the tube has a first lower profile configuration for delivery and a second expanded configuration for placement. The struts extend outwardly so that a distal region of the struts has a greater dimension and the struts define a space therebetween. A mesh material is supported by the struts and provides a blocking member to block the egg from passage through the fallopian tube.

In one embodiment, the mesh material fills a substantial area of the space between the struts. In another embodiment, the mesh material is in the form of a narrow strip attached to one or more of the struts. In another embodiment, the mesh material is attached to an outer surface of the struts, and extends across a proximal region of the device.

A method for fallopian tube occlusion is also provided comprising the steps of inserting into the fallopian tube a sheath containing a retention member having a plurality of struts in a reduced profile position, exposing the retention member from the sheath to enable it to expand to engage a wall of the fallopian tube, subsequently inserting mesh material within a space between the plurality of struts, and withdrawing the sheath to leave the retention member in the fallopian tube so the mesh material fills the space within the tube to occlude the tube.

In one embodiment, the retention member has a plurality of shape memory struts and the step of exposing the retention member enables the struts to move toward a shape memorized position.

BRIEF DESCRIPTION OF THE DRAWINGS

Preferred embodiment(s) of the present disclosure are described herein with reference to the drawings wherein:

FIG. 1 is a perspective view of a the mesh retention member of the fallopian tube occlusion device of the present invention shown in the collapsed position for delivery;

FIG. 2 is a transverse cross-sectional view taken along line 2-2 of FIG. 1;

FIG. 3 is a cross-sectional view taking along lines 3-3 of FIG. 1 showing a portion of the retention member within a delivery sheath;

FIG. 4 is a perspective view showing the occlusion device in the expanded condition without the mesh therein;

FIG. 5 is a view similar to FIG. 4 showing the mesh positioned in the device;

FIGS. 6 and 7 are side and front views of the device of FIG. 5;

FIG. 8 is an anatomical view showing insertion of the delivery device through the uterus of a patient to access the fallopian tubes;

FIG. 9 shows the delivery device being inserted into one of the fallopian tubes;

FIG. 10 is a close up view showing the delivery device within the fallopian tube;

FIG. 11 is a close up view showing the occlusion device deployed in the fallopian tube;

FIG. 14 is an anatomical view illustrating placement of the occlusion device in both fallopian tubes;

FIGS. 15 and 16 are perspective and side views, respectively, of an alternate embodiment of the present invention showing the occlusion device having a strip of mesh supported therein;

FIG. 17 is a side view of another alternate embodiment of the occlusion device having a mesh filling substantially the entire space between the struts;

FIG. 18 is a side view of another alternate embodiment of the occlusion device having a mesh positioned on the outside of the retention member; and FIG. 19 is a perspective view of another alternate embodiment of the occlusion device having a mesh supported by a wound wire.

DETAILED DESCRIPTION OF PREFERRED EMBODIMENTS

Figure 12:
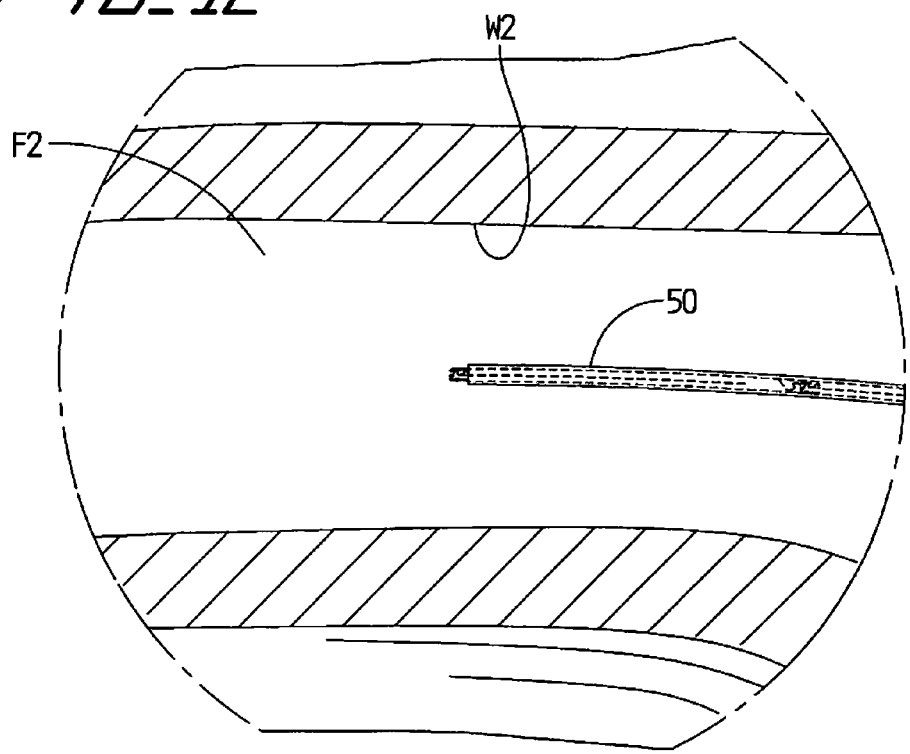
FIGS. 12 and 13 are views similar to FIGS. 10 and 11 except showing placement of the occlusion device in the other fallopian tube.

Referring now in detail to the drawings where like reference numerals identify similar or like components throughout, the several views, an occlusion device for placement in the fallopian tubes for contraception is disclosed. The device can be inserted minimally invasively and preferably in an office procedure. A hysteroscope can be used for direct visualization. The occlusion device includes a securement member and mesh material. The securement member provides for attachment to the fallopian tube as well as a support or retention for the various embodiments of the mesh described below.

With initial reference to FIGS. 1-3 which shows the occlusion device 10 in the low profile collapsed delivery configuration, and FIG. 4, which shows the occlusion device 10 in the expanded placement configuration, the occlusion device 10 includes a securement or retention component (member) 12. Securement member 12 has engagement hooks 14 for engaging the fallopian tube wall to retain the securement member 12 in the tube to prevent migration as described below. The mesh can be advanced into the member 12 in situ or alternatively can be positioned in the securement member 12 in the delivery position and then advanced together with the securement member 12 for placement in the fallopian tube. The occlusion device 10 is preferably formed from a laser cut tube, although other ways of forming the device are also contemplated. The mesh is not shown in FIG. 1-4 for clarity.

Turning to FIGS. 4-7 illustrating the device 10 in the expanded (deployed) position, the retention component 12 is in the form of a bell shaped device with struts as described in detail with respect to the vessel filter disclosed in patent application Ser. No. 10/899,429, filed Jul. 13, 2004, (the '429 application), the entire contents of which is incorporated herein by reference. The device 10 has a proximal end 11a and distal end 11b. Securement member 12 is preferably composed of shape memory material, such as Nitinol, with an austenitic shape memorized position illustrated in FIG. 4 and has a plurality of struts 13 emerging from apex 18 at proximal end 11a and terminating in engaging or retention hooks 14 at distal end 11b. In this embodiment, six struts are provided although a different number of struts is also contemplated. A retrieval hook 16 is positioned on the proximal end 11a to enable the device 10 to be grasped by a snare or other retrieval device and removed if desired. The struts 13 can be interconnected by interconnecting struts 17 which join adjacent struts. More specifically, the struts preferably divide at region 19 into two connecting struts 17, angling away from each other, and then join at region 21 to form extending strut portions 23 terminating in hooks 14. The interconnecting struts 17 stiffen the device to enhance retention and increase the radial force. They also provide a more symmetric and uniform deployment. The hooks are configured to engage the wall of the fallopian tube for maintaining the position of the occlusion device 10. Thus struts are preferably flared and create a distal opening and a space between the struts. For clarity, not all the identical parts are labeled throughout the drawings. It should be appreciated that materials other than Nitinol or shape memory are also contemplated.

The hooks 14 preferably extend substantially perpendicular from the strut, and are preferably formed by torquing the struts so the hooks bend out of the plane. Preferably, a first set of hooks is larger than a second set of hooks. Preferably, when formed from a laser cut tube, the larger hooks are formed so that they occupy a region equivalent to the transverse dimension of two adjacent struts. Preferably, three smaller hooks and three larger hooks are provided in alternating arrangement in the embodiment utilizing six struts. The smaller hooks are preferably spaced axially with respect to each other and axially inwardly with respect to the larger hooks as in the filter hooks of the '429 application to minimize the collapsed profile (transverse dimension) of the filter when collapsed for insertion. The penetrating tips 14a (FIG. 3) preferably point toward the proximal end 11a of the device 10 and penetrate the tissue to retain the occlusion device.

Each of the hooks 14 can have a series of teeth 14c to engage the fallopian tube wall to provide additional retention to prevent movement of the device 10. A heel 14d is provided which extends past the hook to function as a stop to prevent the occlusion device from going through the fallopian tube wall. The angle of the heel 14d in the smaller hooks is less than the angle in the larger hooks to provide room for nesting of the hooks as shown in FIG. 3. For clarity, not all of the hooks are fully labeled.

The securement (retention) member 12 is maintained in a substantially straightened softer martensitic configuration within the delivery catheter or sheath 50 for delivery as shown in FIG. 3. The smaller hooks preferably nest within the larger hooks. Cold saline can be injected during delivery to maintain the device 10 in this martensitic condition to facilitate exit from the distal opening 52 at the distal end portion 54 (FIG. 3) of catheter 50. When the struts 13 exit the delivery sheath (tube 50), they are warmed by body temperature and move toward their illustrated memorized expanded position as shown in FIGS. 4-7.

As shown in FIGS. 8-11 and 14, the device 10 is preferably inserted through the uterus within delivery catheter 50 and into the fallopian tube. It is positioned in this embodiment with the struts opening in a distal direction. When positioned in the fallopian tube, the hooks 14 engage the tube wall to retain the device.

The device 10 in the embodiment of FIGS. 1-7 has mesh material positioned within the retention member 12, filling substantially the entire region of the member 12. A small gap 24 can be left at the proximal region (see e.g. FIG. 6). However, in an alternate embodiment, the gap is filled in with mesh so the mesh fills more of the area between the struts as shown for example in FIG. 17 wherein mesh 61 fills substantially the entire space between the struts 63. Retention member 60 is otherwise identical to retention member 12 of FIG. 1. The mesh is preferably in the form a tightly woven material to provide sufficiently small spaces to effectively block the eggs from the ovaries traveling through the fallopian tube.

The mesh can be delivered within the retention member 12 such that in the collapsed position the mesh is contained and compressed therein. After delivery, it would expand within the space of the retention member 12, i.e. within the space between the struts.

In an alternate embodiment, the retention member 12 would be placed within the fallopian tube first, and then once in place, the mesh would be delivered through the opening in the distal end 11b of the device and within the space between the struts 13 and/or 17. This in situ delivery could occur in embodiments wherein the device 10 is implanted in an orientation opposite to that of FIG. 11, i.e. the opening between the struts would face in the other direction such that the distal 11b would be closer to the uterus than proximal end 11a.

In an alternate embodiment, instead of the mesh filing the space between the struts, the mesh is in the form of a narrow strip. The mesh in this embodiment functions as a screen type blocking member, as shown in FIGS. 15 and 16 and is substantially circular. The retention (securement) member 72 is otherwise identical to securement member 12 of FIG. 1, e.g.

struts 73 divide at region 79 into interconnecting struts 77, join at region 81, and terminate in engaging hooks 74. The strip 85 of mesh would preferably be positioned slightly proximal of the hooks 74, e.g. at the region where the strut twists out of the plane so as not to interfere with the hooks. However, the mesh could be placed at other locations along the struts as long as it functions as a cover or blocking member to occlude the fallopian tube. Although a thin strip of mesh is shown, other size blocking strips could also be provided. The mesh is shown attached to an inner surface of the struts but could alternatively be attached to the outer surface. It could be attached to one or more of the struts.

As noted above, although the retention member is shown inserted with the engaging hooks 14 facing in the distal direction, it is also contemplated that the retention member could be oriented in the opposite direction. In this version (not shown), the mesh can be inserted along with the retention member or alternatively if desired could be delivered in situ within the distal opening between the struts.

In the alternate embodiment of FIG. 18, the mesh 92 is positioned on the outside of the retention member 90. In all other respects, retention member 90 is similar to member 12. In this embodiment, the mesh 92 is placed on an outer region, covering the outer surfaces of the struts and apex region and interposed between the struts and the fallopian tube when placed. Thus, the mesh functions as a sleeve which prevents passage of the eggs as they would be captured within the sleeve or net-like device.

The mesh in the foregoing embodiments can be attached to the retention member by various methods such as bonding, clamping and suturing.

The method of placement of the occlusion device of the present invention will now be described for occluding a fallopian tube and with reference to FIGS. 8-14 which illustrate by way of example the device of FIG. 5 with the mesh delivered in conjunction with the securement member (the other embodiments are inserted in a similar fashion). A delivery catheter 50 is inserted through an introducer sheath 100 through the vagina and cervix into the uterus U. The catheter 50 is then advanced into fallopian tube F1. For insertion, the retention member 12 (and mesh) is in the collapsed position.

Figure 13:
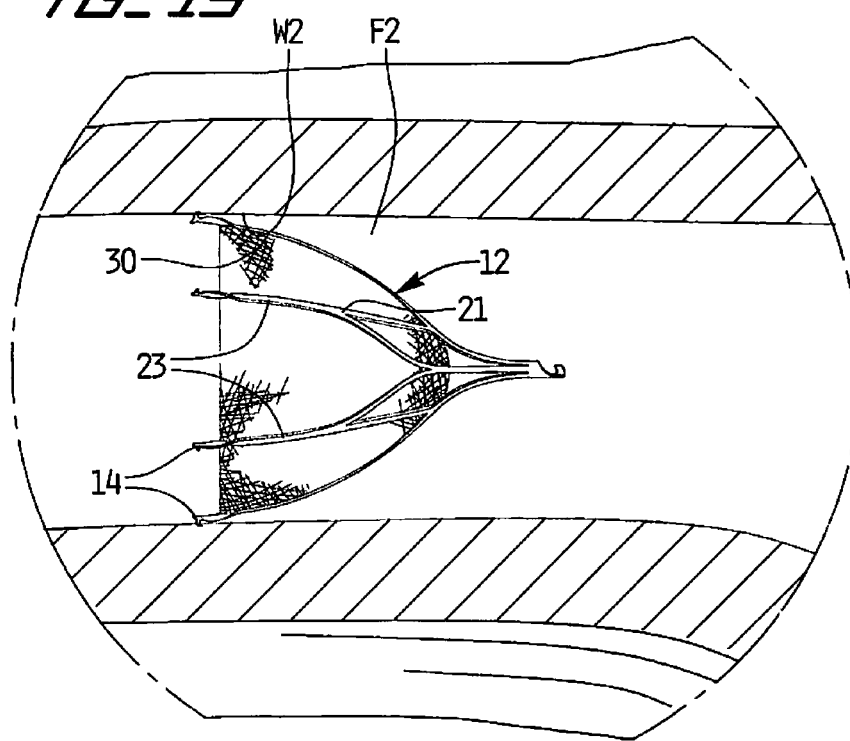

A pusher (not shown) is advanced distally to advance the occlusion device 10 from the catheter 50. As the struts of device 10 are exposed, they are warmed by body temperature and return toward their shape memorized deployed position as shown in FIG. 11 to engage the wall W1 of the fallopian tube. The extent they return to their fully memorized position will depend on the size of the fallopian tube. The catheter 50 is then withdrawn into the uterus and inserted into fallopian tube F2 (FIG. 12) (or another catheter is used) wherein another occlusion device 10 is exposed from the catheter 50 so the struts move to the expanded position to engage the wall W2 of tube F2 as illustrated in FIG. 13. The expanded mesh functions to block the travel of eggs through the tube.

As can be appreciated, although described for closing the fallopian tube, the occlusion device can be used in other areas of the body.

Note, the material inside or outside the retention member could be non-porous or porous. It could alternatively be made of pericardium, SIS, PET, PTFE, or other materials.

In the alternate embodiment of FIG. 19, a wound wire 100 provides a support member for mesh 110. The wire as shown has a substantially conical mesh so the diameter (transverse dimension) at region 112 exceeds the diameter (transverse dimension) at region 114. The mesh 110 is provided on an outer surface as shown. Alternatively, the mesh could be positioned inside or a strip of mesh spanning the opening could be provided. The wire could have hooks, barbs or other surfaces to enhance retention in addition to the outward radial force against the fallopian tube wall.

While the above description contains many specifics, those specifics should not be construed as limitations on the scope of the disclosure, but merely as exemplifications of preferred embodiments thereof. For example other materials can be contained or mounted to the retention member to function to block eggs from passage through the fallopian tubes. Those skilled in the art will envision many other possible variations that are within the scope and spirit of the disclosure as defined by the claims appended hereto.

What is claimed is:

1. A method for fallopian tube occlusion comprising the steps of:
    inserting into a fallopian tube a sheath containing a retention member having a plurality of struts in a reduced profile position;
    exposing the retention member from the sheath to enable the struts to expand to an expanded position to engage a wall of the fallopian tube;
    subsequently inserting mesh material within a space between the plurality of struts in the expanded position in situ; and
    withdrawing the sheath to leave the retention member in the fallopian tube so the mesh material fills the space within the struts to block passage of an egg through the fallopian tube.

2. The method of claim 1, wherein the retention member has a plurality of shape memory struts and the step of exposing the retention member enables the struts to move toward a shape memorized position.

* * * * *